United States Patent [19]
Yang

[11] Patent Number: 5,104,626
[45] Date of Patent: Apr. 14, 1992

[54] VIBRATING DIFFUSION TYPE AROMATIC DEVICE

[76] Inventor: Tai-Her Yang, 5-1 Taipin St., Si-Hu Town, Dzan-Hwa, Taiwan

[21] Appl. No.: 579,395

[22] Filed: Sep. 7, 1990

[51] Int. Cl.$^5$ ............................................. A61L 9/00
[52] U.S. Cl. ................................. 422/124; 422/305; 417/436
[58] Field of Search ................ 417/411, 436; 422/124, 422/123, 120, 5, 305

[56] References Cited

U.S. PATENT DOCUMENTS

| | | | |
|---|---|---|---|
| 3,351,933 | 11/1967 | Maltby et al. | 310/25 |
| 4,063,826 | 12/1977 | Rieke | 417/436 |
| 4,219,531 | 8/1980 | Wisniewski | 417/411 |
| 4,753,379 | 1/1988 | Murphy | 417/410 |

Primary Examiner—Richard A. Bertsch
Assistant Examiner—David W. Scheuermann
Attorney, Agent, or Firm—Leonard Bloom

[57] ABSTRACT

A vibrating diffusion type aromatic device is disclosed. The device includes a vibrating unit including a magnetic reed. An aromatic plaque having an aroma is mounted on the reed. A magnetic device including a coil for attracting the magnetic reed for spreading the aroma under vibration. A vibrating operation circuit is provided to drive the coil and vibrate the reed.

3 Claims, 1 Drawing Sheet

VIBRATING DIFFUSION TYPE AROMATIC DEVICE

FIELD OF THE INVENTION

The present invention relates to diffusion type aromatic devices, and in particular, to a device that has an electric magnet, a reed including an aromatic plaque thereon and a vibrating circuit to control the magnet to move the reed for spreading or dispersing the aroma of the aromatic plaque into air.

BACKGROUND OF THE INVENTION

Conventional diffusion type aromatic devices usually use a rotary motor to drive a fan which provides air flow for spreading aromatic odors into the air for improving air quality. As the fan is a motion type element, it needs a motor and rotary blades. These requirements increase the cost and the dimensions of those devices.

SUMMARY OF THE INVENTION

In accordance with the teachings of the present invention, a vibrating diffusion type aromatic device is provided. In this device, an aromatic plaque is disposed on a magnetic reed and a coil periodically attracts the reed in order to move (vibrate) the reed in order to spread the aroma into the air. The vibrating diffusion type aromatic device according to the present invention effectively reduces the production costs, as well as the dimensions and weight of such devices.

DETAILED DESCRIPTION OF THE INVENTION

Aromatic devices are widely utilized in the car, office, private rooms and bathrooms to create a more pleasant aromatic environment. However, most of such devices include a motor for driving a fan that spreads aroma. The production of such devices cannot be accomplished at a reasonable cost and having reasonable dimensions. The present invention provides a vibrating diffusion type aromatic device comprising a power supply, a vibrating unit, an aromatic plaque and a housing. Such a device may have small dimensions, so that it can be made portable, desk top size or hanging size for convenience of use.

The structure of the device of the present invention is hereafter described.

Figure 1:
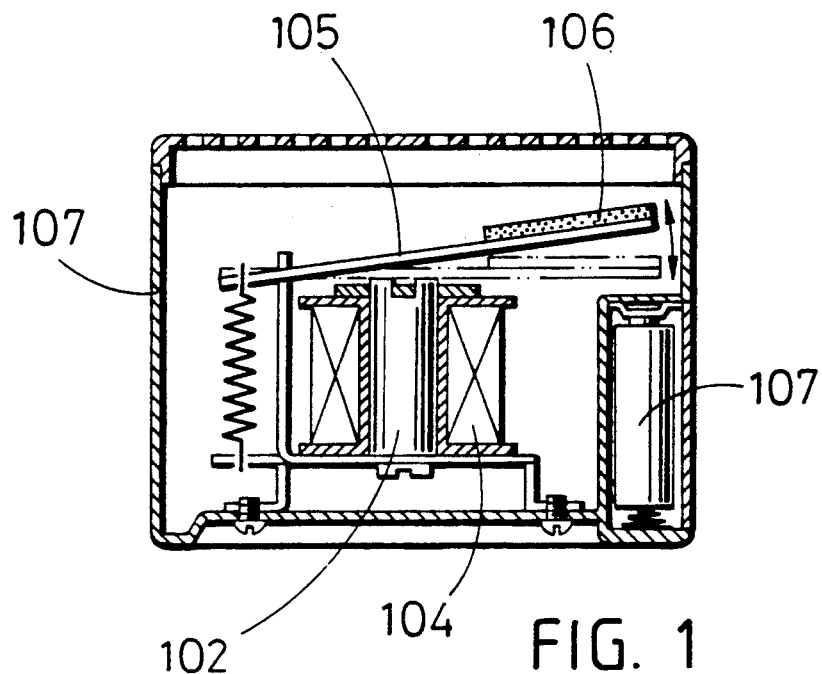
FIG. 1 is a side view, in cross-section, of the vibrating diffusion type aromatic device of the present invention.

Referring to FIG. 1, the device has a power supply 101, including a battery assembly or an AC circuit or a rectified DC circuit. A magnetic device 102, including a coil 104, is provided for periodically attracting (vibrating) a magnetic reed 105 which has mounted thereon an aromatic plaque 106 having an aroma for being spread under vibration. A vibrating operation circuit is provided to periodically attract (drive or oscillate) the coil 104. Finally, a housing 107 is provided. Upon power transmission, the magnetic reed 105 may be periodically attracted (vibrated or oscillated) in a continuous manner (at a super low frequency generally being below 20 HZ) to spread aroma into the air.

Figure 2:
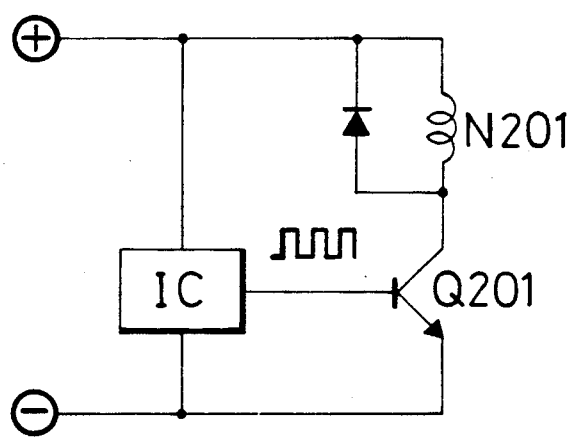
FIG. 2 is a circuit diagram showing a first embodiment of an electrical circuit for the device of FIG. 1.

Referring to FIG. 2, the vibration operation circuit is operated by periodic pulses, wherein periodic pulse IC generates a periodic ON/OFF signal to drive SW (switch) transistor Q201 and further to provide the coil N201 with power for periodically attracting (vibrating or oscillating) the magnetic reed 105, so that the reed 105 moves (vibrates or oscillates) in order to spread the aroma of the aromatic plaque mounted on the reed 105.

Figure 3:
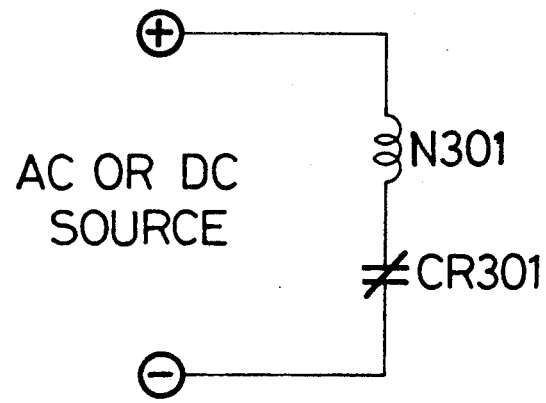
FIG. 3 is a circuit diagram showing a second embodiment of an electrical circuit for the device of FIG. 1.

Referring to FIG. 3, another embodiment of the vibration operation circuit is seen to be operated by a frequent closed contact assembly CR301, wherein the movement of the reeds breaks the circuit during attraction, and wherein during the rebound of the reeds to form a closed contact assembly for driving the coil N301 in free vibration to spread the aroma of the aromatic plaque on the reeds.

To conclude, the vibrating diffusion type aromatic device of the present invention has an aromatic plaque that is mounted on the reeds and a coil that periodically attracts the reed in order to move (vibrate) the reeds in order to spread the aroma in substitute for the conventional spreading type by fan motor. Thus, production of such an aromatic device can be accomplished at reasonable costs and dimension.

We claim:

1. A vibrating diffusion type aromatic device comprising a power supply, a vibrating unit including a magnetic reed, an aromatic plaque mounted on the magnetic reed, the aromatic plaque having an aroma, and a housing, and a magnetic device including a coil for attracting the magnetic reed on which is mounted the aromatic plaque for spreading the aroma under vibration, and a vibrating operation circuit provided to drive the coil, whereby the reed is continuously vibrated at a frequency being below 20 HZ to spread aroma into the air.

2. A vibrating diffusion type aromatic device comprising a power supply, a vibrating unit including a magnetic reed, an aromatic plaque mounted on the magnetic reed, the aromatic plaque having an aroma, a housing in which the power supply, the vibrating unit and the aromatic plaque are housed, a magnetic device including a coil for attracting the magnetic reed on which is mounted the aromatic plaque for spreading the aroma under vibration, and a vibrating operation circuit provided to drive the coil, whereby the reed is continuously vibrated at a frequency being below 20 HZ to spread aroma into the air, and further wherein the circuit being operated by periodic pulse, and periodic pulse IC generating a periodic ON, OFF signal to drive switching transistor and further to provide the coil with power for attracting the magnetic reed to vibrate for spreading the aroma of the aromatic plaque that is mounted on the reed.

3. A vibrating diffusion type aromatic device comprising a power supply, a vibrating unit including a magnetic reed, an aromatic plaque mounted on the magnetic reed, the aromatic plaque having an aroma, a housing in which the power supply, the vibrating unit and the aromatic plaque for spreading the aroma under vibration, and a vibrating operation circuit provided to drive the coil, whereby the reed is continuously vibrated at a frequency being below 20 HZ to spread aroma into the air, and wherein the vibrating operation circuit is further operated by a frequent closed contact assembly for driving the coil to provide for vibration of the magnetic reed to spread the aroma of the aromatic plaque.

* * * * *